US011152120B2

(12) United States Patent
Britt et al.

(10) Patent No.: US 11,152,120 B2
(45) Date of Patent: Oct. 19, 2021

(54) IDENTIFYING A TREATMENT REGIMEN BASED ON PATIENT CHARACTERISTICS

(71) Applicant: International Business Machines Corporation, Armonk, NY (US)

(72) Inventors: Michael Britt, Rochester, MN (US); Adam C. Lange-Pearson, Rochester, MN (US); Fernando Jose Suarez Saiz, Armonk, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 84 days.

(21) Appl. No.: 16/212,953

(22) Filed: Dec. 7, 2018

(65) Prior Publication Data

US 2020/0185099 A1 Jun. 11, 2020

(51) Int. Cl.
*G16H 50/20* (2018.01)
*G16H 10/60* (2018.01)
*G16H 50/70* (2018.01)
*G16H 70/20* (2018.01)
*G06F 16/2457* (2019.01)

(52) U.S. Cl.
CPC ....... *G16H 50/20* (2018.01); *G06F 16/24575* (2019.01); *G16H 10/60* (2018.01)

(58) Field of Classification Search
CPC ........ G16H 50/20; G16H 10/60; G16H 40/67; G16H 40/63; G16H 40/20; G06F 16/24575; G06F 16/2455; G06Q 10/06; G06Q 10/10

See application file for complete search history.

(56) References Cited

U.S. PATENT DOCUMENTS

| 8,645,396 | B2 * | 2/2014 | McNally | G06F 16/9535 |
| | | | | 707/748 |
| 10,176,541 | B2 * | 1/2019 | Chaudhri | G06Q 50/22 |
| 2004/0044547 | A1 | 3/2004 | Klennert | |
| 2005/0216307 | A1 * | 9/2005 | Clements | G06Q 50/22 |
| | | | | 705/2 |
| 2007/0143273 | A1 | 6/2007 | Knaus | |
| 2008/0215570 | A1 | 9/2008 | Maloney | |
| 2009/0063428 | A1 * | 3/2009 | Meier | G16H 10/20 |
| 2012/0041772 | A1 * | 2/2012 | Ebadollahi | G16H 50/70 |
| | | | | 705/2 |

(Continued)

OTHER PUBLICATIONS

E. Ecker. "Conducting a Winning Literature Search." Evidence-Based Spine-Care Journal 1.1 (2010): 9-14. PMC. Web. May 4, 2018.

(Continued)

*Primary Examiner* — Eliza A Lam
(74) *Attorney, Agent, or Firm* — Steven L. Nichols; Fabian VanCott

(57) ABSTRACT

A method of searching a database of medical research for documentation in support of a specific treatment for a patient, the method including: identifying a medical condition; identifying attributes of the patient; searching the database for treatment regimens for the medical condition; scoring identified treatment regimens based on similarity of the attributes of the patient to cohorts treated with the treatment regimens and outcomes; and providing a recommendation for a treatment regimen for the patient based on the attributes of the patient.

20 Claims, 4 Drawing Sheets

(56) References Cited

U.S. PATENT DOCUMENTS

2012/0072232 A1* 3/2012 Frankham .............. G16H 10/20
705/2
2013/0254178 A1 9/2013 Srivastava
2013/0268538 A1 10/2013 Nelson

OTHER PUBLICATIONS

W. Bramer, "Optimal Database Combinations for Literature Searches in Systematic Reviews: A Prospective Exploratory Study." Systematic Reviews 6 (2017): 245. PMC. Web. May 4, 2018.
S. Wong, "Developing Optimal Search Strategies for Detecting Clinically Sound Treatment Studies in EMBASE." Journal of the Medical Library Association 94:1 (2006): 41-47.
A. Krishnan, "Search for patents using treatment and causal relationships." In Proceedings of the 3rd international workshop on Patent information retrieval (PaIR '10). ACM, (continued)New York, NY, 1-10, 2010.

* cited by examiner

200

Treatment Regimens for MEDICAL CONDITION for
PATIENT NAME having the following medical considerations:
    PATIENT FACTOR 1
    PATIENT FACTOR 2    220
    PATIENT FACTOR 3

Edit Factors
232

226

| | |
|---|---|
| B 222 | Outcome: 52%   Reliability: 75%   Relevance: 45%<br>Treatment 1: Radiation XX fractions for a total dose of Y gray over Z weeks    224<br>Citations  ← 228 |
| C+ | Outcome: 65%   Reliability: 20%   Relevance: 20%<br>Treatment 2: Chemotherapy with Medication XXX at dosing regimen YYY.   EXPERIMENTAL!<br>Citations |
| C | Outcome: 55%   Reliability: 60%   Relevance: 30%<br>Treatment 3: Combination chemotherapy with Medication XXX at YYY dose per treatment<br>Citations |
| C | Outcome: 30%   Reliability: 80%   Relevance: 58%<br>Treatment 4: Secondary surgery to provide clean margins.<br>Citations |
| D | Outcome: 10%   Reliability: 80%   Relevance: 65%<br>Treatment 5: Watchful waiting<br>Citations |

230

| Sort by Outcome | Sort by Reliability | Sort by Relevance |

*Fig. 2*

IDENTIFYING A TREATMENT REGIMEN BASED ON PATIENT CHARACTERISTICS

BACKGROUND

The present invention relates to personalized medicine, specifically, to identifying a treatment regimen for a patient with a first medical condition based on other medical conditions and demographic information of the patient.

SUMMARY

In one embodiment of the present invention describes a computer-implemented method of searching a database of medical research for documentation in support of a specific treatment for a patient. The method includes identifying a medical condition. The method includes identifying attributes of the patient. The method includes searching the database for treatment regimens for the medical condition. The method includes scoring identified treatment regimens based on similarity of the attributes of the patient to cohorts treated with the treatment regimens and outcomes. The method includes providing a recommendation for a treatment regimen for the patient based on the attributes of the patient.

The scoring may include an assessment of article quality. The assessment of article quality may include a number of citations to the article. The scoring may include an assessment of publication quality.

The method may further include, when the amount of search results are outside a window, modifying parameters of the search and repeating the search. The method may include documenting the search parameters and results to guide future searches.

This specification also describes a computer program product for identifying a treatment regimen for a patient based on medical conditions of the patient and demographic information of the patient. The computer program product may be a computer readable storage medium having program instructions. The computer readable storage medium is not a transitory signal per se. The program instructions are readable by a computer to cause the computer to perform a method. The method includes identifying a medical condition of the patient for which the treatment regimen is being identified. The method includes identifying demographic information for the patient. The method includes identifying other medical conditions of the patient. The method includes searching a database for publications related to the medical condition of the patient. For each identified publication, the method includes categorizing the publication to a treatment regimen and rating the publication on three scales. The first scale being the reliability of the publication, the second scale being outcomes of the treatment regimen on a studied cohort, and the third scale being the relevance of the studied cohort to the patient. The method further includes combining data from multiple publications into an assessment of a treatment regimen. In an example, the combined data is a current standard of care.

A publication may include results for more than one treatment regimen. For example, a control arm may be a standard of care treatment and a test arm may be a second treatment regimen. The relevance rating may consider comparison of patient characteristics including patient demographic information and medical conditions with exclusion and inclusion conditions from the publication. The method may further include sorting treatment regiments by an elected scale of the three scales. The rating of reliability may consider a cohort size documented in a publication. The method may exclude a publication comprising a data set or a meta-analysis the data set when a publication comprising the data set or meta-analysis is included.

The method may further include saving search parameters and outcomes of the search and modifying parameters of a subsequent search based on an outcome of the search.

This specification also describes a computer program product for identifying a patient specific treatment regimen. The computer program product includes a computer readable storage medium having program instructions. The program instructions are readable by a processor and when executed cause the processor to perform the following operations. The processor extracts patient information from a record. The record may be a patient's medical history. The processor identifies a medical condition for which a treatment regimen is being sought for the patient. The medical condition may be flagged by a medical professional. The medical condition may be identified by the patient. The medical condition may be identified based on the patient's medical records. The processor scores studies in a database based on similarity between the information of the patient and a cohort receiving a treatment regimen in the study. The information may include medical conditions as well as demographic information. The processor recommends a treatment regimen based on an outcome from the treatment regimen in the study and correlation between the patient and the cohort receiving the treatment regimen in the study. Both the effectiveness of the treatment regimen and the relevance of the cohort to the patient are used to determine whether to recommend a regimen.

In an example, the scoring considers the size of the treatment cohort when scoring a study. The scoring may consider statistical results (e.g., p-values) when scoring a study.

BRIEF DESCRIPTION OF THE SEVERAL VIEWS OF THE DRAWINGS

FIG. 2 shows an example of an interface for a system consistent with this specification.

DETAILED DESCRIPTION

Figure 1:
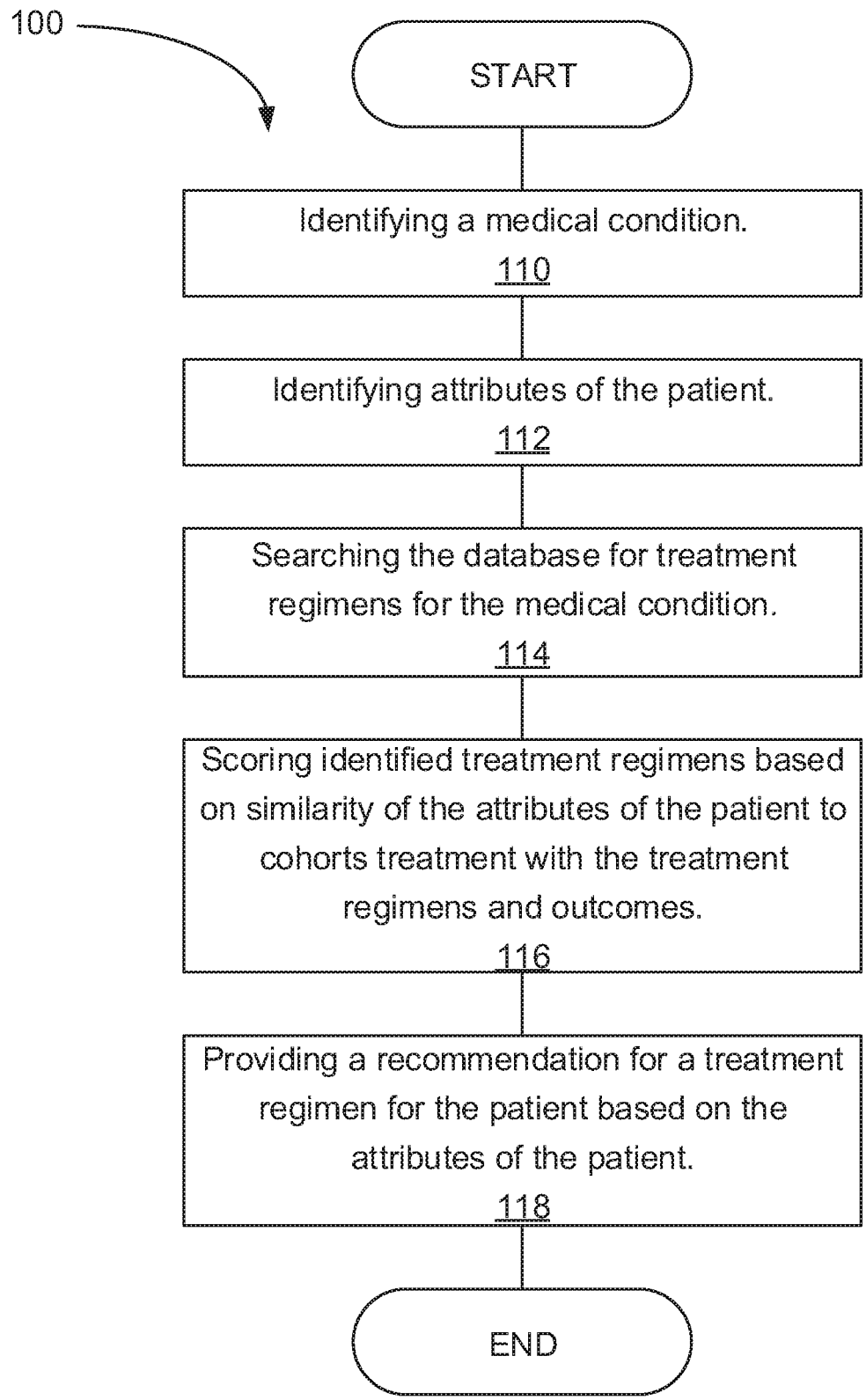
FIG. 1 shows a flowchart of a computer-implemented method of searching a database of medical research for documentation in support of a specific treatment for a particular patient consistent with this specification.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Turning now to the figures. FIG. 1 shows a flowchart for a computer-implemented method (100). The method (100) including: a processor identifying (110) a medical condition of a patient; the processor identifying (112) attributes of the patient; the processor searching the database for treatment regimens for the medical condition; the processor scoring (114) identified treatment regimens based on outcomes and similarity of the attributes of the patient to cohorts treated with the treatment regimens; and the processor providing (116) a recommendation for a treatment regimen for the patient based on the scoring.

This approach method (100) recognizes that the medical literature disproportionately reports normative cohorts which may exclude a variety of conditions. Medical literature also may be highly disproportionate on ethnicity, age, and other factors when predicting outcomes. For example, drug safety trials are generally performed on healthy college-age persons without comorbidities. Similarly, blood tests and other procedures tend to be developed on healthy individuals. Even when clinical trials are conducted, exclusion criteria often limit the ability to extrapolate the data to other types of patients.

While useful for initial work in demonstrating effectiveness of a treatment regimen, this approach may hide risk to patients who have cofactors such as high blood pressure, age, etc. The described computer-implemented method (100) builds on the idea of personalized medicine. Personalized medicine is the idea of tailoring the treatment regimen to the characteristics of the patient. In many uses, the characteristics of the patient are used as shorthand for specific genetic markers possessed by the patient. The mutation of the BRCA 1 and 2 genes is an example of using patient characteristics to modify treatment (e.g., use of estrogen in treating breast cancer). However, a variety of non-genetic conditions should also be considered when assessing the impact of treatment regimens. These conditions include other medical conditions of the patient, age, smoking history, etc.

Tailoring treatments by patient attributes is challenging. While the default treatments for a condition may be readily determined, documentation of subgroups and atypical cohorts tend to be harder to find and smaller in number. In some examples, case reports, letters, and retrospective analysis will be the most common form of data instead of blind, randomized studies. Accordingly, there is a tendency for systems to default to the default treatment and ignore patient specific factors. However, as the amount of information available in medical databases increases, the prevalence of case reports and small studies which look at different conditions also increases.

Perhaps the most obvious patient condition is age. For example, few medical studies look at minors for a variety of reasons, including concerns about liability, market size, etc. The result is that the literature tends to lack effective information on the medical response of minors to medications. Indeed, FDA has a special program to provide additional market protection for medications that obtain trial data on minors. In many cases, however, minors are treated as little adults and extrapolation is based on proportional body weight and/or other factors. This occurs despite the accepted medical understanding that continued development in children impacts a wide variety of healing and biological responses. When seeking information on treatment options for pediatric patients, the general information from population studies is useful, but flagging and identifying any pediatric specific results in beneficial.

Another major patient condition that is underrepresented in the literature is pregnancy. Again, for a variety of reasons, pregnant women have been excluded from developing procedures and/or medications. While this serves to minimize the risk, it also produces a lack of data on the interaction of many medical treatments with pregnancy. This presents a challenge for a physician when trying to determine an appropriate course of treatment for a pregnant patient as the studies will rarely be representative of their patient. As with pediatric medicine, a large number of therapies are performed off-label and/or based on best medical evidence rather than proper studies. Tracking down any evidence of outcomes in such cases is useful for determining the best medical evidence when recommending a course of treatment.

At the other end of the age spectrum, older individuals show variation from the younger population in healing response and other relevant factors. Further older individuals are more likely to have accumulated other medical diagnosis which be relevant to recommending a treatment regimen. In some cases, studies, especially retrospective studies, are available to evaluate the results of treatment regimens when other medical conditions are present. In some cases, a primary treatment regimen is contraindicated for patients with a secondary condition. For example, some medications are not recommended for patients with high blood pressure.

Accordingly, it is useful to identify patient specific treatment information when determining a treatment regimen for the patient. Because such modified treatment regimens are by definition not the default treatment, they generally have lower publication rates and data availability. Identifying and characterizing the published information on treatment of atypical patients is challenging for a number of reasons. First is the reduced prevalence, discussed above. Second is the confounding of terms with the primary treatment regimen and/or cohorts. Third is the lack of standardized terminology for many atypical cohorts. However, while this information is difficult to acquire, this type of information is also valuable in providing personalized treatment for patients. To the degree this information can be effectively collated and provided to patients and medical professionals, patients may have more information and/or higher confidence about the likely outcomes of a treatment regimen.

The method (100) includes a processor identifying (110) a medical condition. The medical condition is to be treated by the recommended treatment regimen. The medical condition may be a disease. The medical condition may be a condition. The medical condition may be expressed broadly (e.g. cancer) and/or narrowly (Stage 2, small-cell, lung cancer of one lobe). The medical condition may be selected from a pull down menu. The medical condition may be selected from search results.

The method (100) includes the processor identifying (112) attributes of the patient. In an example, this includes extracting the attributes from a patient medical record. The patient medical record may be an electronic record and/or a paper file. The method may include standardizing terminology in the medical record. The method may include calculating age from a birthdate and/or other record.

The attributes may be reviewed by a user. In an example, the patient reviews the attributes, for example, as part of an intake process. The attribute may be reviewed by a medical provider. In some examples, the attributes may be elected from pulldown lists and/or search results. In an example, the results of an intake form and/or a medical history may provide the attributes. The system may calculate attributes, such as Body Mass Index (BMI) and/or age. The system may estimate socio-economic status (SES) data from an address and/or zip code.

The method (100) includes the processor searching (114) the database for treatment regimens for the medical condition. The searching may include identifying studies of different treatment regimens.

The database may be a database of medical literature. The database may be a database of journal articles. The database may include clinic trial results. The database may include summaries and/or retrospective analysis from patient data at the institution requesting the result. For example, a given institution may have a higher rate of surgical success compared with national averages which justify a higher rating of surgical options as recommended treatment regimens. For example, an institution may have reduced positive outcomes for radiation therapy due to serving a patient base which lives far from the institution and has reduced rates of compliance. This may justify reducing the recommendation for radiation therapy for patients living far from the treatment facility. While more difficult to process, such outcomes from local treatment by the same institution may be highly predictive compared with national and/or international studies.

In an example, the system may combine results for a shared treatment regimen from different sources prior to scoring. The system may score the individual sources and then produce a combined weighting. Such a combination may increase the reliability rating based on the sum of the number of patients in multiple sources. This approach may be particularly useful when there is an existing standard of care. In some examples, scoring of different sub-values may be performed based on different factors and/or weightings. For example, the reliability may be based on the total number of patients while the effectiveness may be based on a weighted average of results. Similarly, relevance to the patient may be assessed using a weighted average. The weightings may be based on the number of patients in the relevant treatment cohorts of the respective publications.

The method (100) includes the processor scoring (116) the treatment regimens based on similarity of the attributes of the patient to cohorts treated with the treatment regimens and outcomes. The system may identify a treatment cohort in a publication and extract demographic and/or medical profile information from the study. The system may extract exclusion criteria to define the cohort. The system may identify mean age. The system may identify cofactors and/or other conditions in the cohort. The scoring of the treatment regimens may include generating sub-scores.

A variety of methods may be used to score and assess the relevance of the cohort to the patient. When the cohort includes range data for a factor such as age, the patient may match the cohort if within the range. The patient may match the cohort if within the inclusion criteria for that factor. For example, if a cohort had an exclusion criterion of less than 40 years of age and actual patients of ages 46 to 72, a patient of age 42 could be considered within the cohort or outside the cohort depending on the approach selected. Alternately, the rating may be tiered for such situations. For example, a discount factor to the weighting may be applied based on the difference from the mean of the cohort and the standard deviations from the mean. For example, a patient with an age within +/− one standard deviation of the median age may be assigned a weighting of 1, indicating high relevance and no discount. A patient with an age between one and two standard deviations may be assigned a weighting of 0.8 indicating a small discount. A patient with an age between two and three standard deviations may be assigned a weighting of 0.5 indicating a substantial discount. Patients outside of three standard deviations may be assigned a low weighting (i.e., high discount factor), for example, 0.2 to 0. Similarly, inclusion criteria, cohort range, and other reported factors may be used to provide weightings to the relevance of the cohort to the patient. The discount could be produced using a formula to produce continuous weightings and differentiate between, for example, 0.1 standard deviations and 0.8 standard deviations. A preferred distribution would be relatively high and flat over the patients in the cohort and then taper off outside the reported range. It is useful to remember that just because a cohort includes a subpopulation with a characteristic that the study may not have been powered to detect variation on that subpopulation. Accordingly, the extremes of a cohort may be discounted compared to the main body of the cohort to reflect the reduction in detection power.

In some instances, the actual distribution of patient variables may be available. In such cases, that data can be used to determine the comparison between the cohort and the patient, for example, using a sum least squares or average sum least squares measurement. Such a result may then be scaled to a 0 to 1 weighting factor. In some examples, the median and or mean result is reported along with a standard deviation. Sometimes a minimum and a maximum are also reported. In one example, it is useful to simulate the actual distribution of the population using the median and/or mean and the variation. For example, a normal distribution may be assumed and a population randomly generated. This can be helpful to incorporate the distribution information when using a cluster matching approach as described below.

The assessment of relevance of the cohort and patient may be determined using Principle Component Analysis (PCA). If available, each cohort patient is put into an N-dimensional array of factors, e.g., age, sex, condition1, condition2, etc. If the patient data is not available, a number of simulated cohort patients may be generated which reflect normal distribution and the known factors. This approach of using simulated patients may be especially useful when combining multiple studies. One simulated population for a first study is generated. A second simulated population for a second study is generated. The multiple simulated populations may then be combined and a meta result as well as a relevance to the whole simulated population determined. Once the N-dimension array is prepared either from actual and/or simulated data, PCA is used to extract the principle component. The principle component is a vector with a weighting for each dimension of the array of factors. The principle component may then be applied to the patient's data to determine how typical the patient is compared with the cohort. This provides an example of an objective way to assess relevance of the patient and cohort. In some instances the N-dimensional array of factors is also populated with a control group of patients. Instead of using the principle component, the patient is compared against the vector of person in the cohort. That is to say, participation in the study (or having the identified condition for which treatment is being sought) is assigned to a row in the array and then a component for that row is calculated using PCA to assess how the cohort population differs from the provided control population. This introduces more variation from the control population but has the advantaged of not deweighting properties and/or factors that are highly common in the patient population.

One advantage of this PCA based approach is that the calculation and analysis may be performed in advance and the vector of factors stored in a database. Once the patient information is provided, the relevance may be rapidly calculated from the patient information and the vector of factors to provide a relevance weighting. This pre-calculation avoids delay between acquiring the patient data and being able to provide the relevance information for the patient. Indeed, the time to provide a relevance assessment after the patient data is available and verified may be on the order of the time required to access the database. In one example, the database is available over a network and the request time to retrieve the vector is the largest time in the process of calculating the relevance. As this can be on the order a under a few seconds, the whole process may be performed as part of a discussion with a medical professional or as a point of care device.

In another approach the various factors are assigned a simple match/no match value against the cohort and the resulting sum is scaled to a weighting factor. For example, if there are a total of 30 demographic and/or condition factors, a score of 15+ may be scaled to a weighting of 1 and scores 5 or less scaled to a weighting of 0 with scores between 5 and 15 scaled to weightings between zero and one. This approach is simpler to implement than the PCA based approach above and has the advantage of being easier to automate as match or no-match may be determined using keyword or other machine-implementable techniques.

The method (100) includes the processor providing (118) a recommendation for a treatment regimen for the patient, wherein the recommendation identifies a supporting reference. The system selects the recommendation based on the relevance of the results of the data in the references to the patient. The recommendation may be based on the outcomes (benefit) and/or the reliability of the studies. The method may present a set of ordered recommended treatment regimens based on the scoring. The recommendations may be assigned a letter, number, or other indicator to reflect the scoring, both overall and by sub-score. For example, treatment regimens and/or subfactors rankings may be presented using a variety of scoring systems, for example: A through F, 1 to 5 (stars and/or other symbols), 1 to 100, by colors, e.g., green, yellow, red, etc. In an example, a book icon is used for reliability, a plus icon is used for benefit, and a stick figure is used for relevance.

The method may include scoring time commitment and/or recovery time, treatment type (oral, injection, outpatient, inpatient, surgery, etc.), side effects, risk, cost, and/or other sub-factors. In some examples, these sub-factors are not included in the overall recommendation. In an example, each of the sub-factors is included in the final recommendation.

In an example, much of the analysis is done beforehand, including extraction of the published results, and determination of cohort data. After the patient's conditions and attributes are identified, the determination of relevance to the patient and overall scoring may be finalized. The system may include a database of regimens and data supporting those studies. The system may perform periodic sweeps of a publication database to update the study database. In some examples, the study database is curated. In an example, the study database is crowd-sourced.

In an example, the scoring includes an assessment of article quality. For example, this may include the number of citations to the article, the publication quality, the recentness of the article. Article may consider institutional affiliation. Article quality may consider professional associations.

In some examples, the search results will produce a very large or very small number of references. For example, searching for cancer treatments will produce a very large number of references while searching for pediatric stomach cancer stage 2 will produce a small number of references. When the number of returned references is outside a window, the system may modify the search (either removing and/or including additional terms) to attempt to center the number of identified references within a window. In some examples, the system processes an identified small number of references and then expands the number of references by searching the terms while removing one patient factor at a time.

In an example, the system may request additional patient factors or limitations from a user. For example, if the system is not provided with patient information, the system may prompt for patient data and/or request an explicit command to run the search without patient information. As all patients have at least an age, it follows that all patients have at least some potentially relevant attribute to consider when evaluating published study results.

The system may save the search parameters to guide future searches. The system may save a list of citations to guide future searches. The system may save processed and/or partially processed information on publications to guide future searches. Storing processed/extracted studies in a database and/or similar structure may reduce response time to requests.

FIG. 2 shows an example of an interface for a system (200) consistent with this specification. The interface includes: a set of patient factors (220), a set of treatment regimens (224) with a rating for each treatment regimen (222). Each treatment regimen also includes subratings (226), in this example for Outcome, Reliability, and Relevance. A hypertext link (228) to a list of citations is available for each treatment regimen (224). Near the bottom, buttons exist to modify the sorting order (230) by different ratings and/or subratings. A button (232) allows also user to edit the patient factors (220). These different features may be combined in different sets to form interfaces with more or fewer options and more or less visual information.

Each of the treatment regimens (224) may be defined with a set of medical interventions. These may range from surgical options, medications, therapies, etc. to continued follow up with a medical professional. In some cases, hospice care and/or pain management are available treatment regimens (224). Generally speaking, No Action is not considered a treatment regimen (224) but may be provided in the list as a control and/or reference to provide a patient with a greater sense of what options are available.

In the example of FIG. 2, a number of treatment regimens (224) are shown for what appears to be post resection treatment of a tumor bed. The ratings provided are merely exemplary and not based on actual data. Based on Treatment 4, it is inferred that there was an incomplete margin during the resection. The patient has a number of different treatment options available. For example, Treatment 1 is a course of radiation therapy, Treatment 2 is a round of chemotherapy, Treatment 3 is a different type of chemotherapy, Treatment 4 is surgical, and Treatment 5 is watchful waiting. In some examples, there may be a large number of options of a given type. For example, there may be many different types of chemotherapy regimens. Similarly, there may be many options for radiation therapy. In some cases, the system presents just the highest rated option for a type of therapy to avoid overloading the patient. In an example, selecting a type of therapy provides a similar display focused on the options in a treatment area. For example, clicking on Treatment 2 may display a number of different chemotherapy options.

Each treatment regimen (224) has an overall rating (222) displayed. In some examples, this overall rating (222) is displayed prominently as shown, for example, in a larger text, in a contrasting color, etc. The overall rating (222) may be have limited precision to provide easier comparison of treatment regimens (224). In FIG. 2, the overall rating is given a letter grade. In some examples, the range of displayed options is expanded so that options covering the entire range are presented. For example, the B could be scaled to an A and the D scaled to an F. This would provide further resolution between Treatments 2 through 4. The overall ratings (222) may use a portion of the range of the rating scale. This approach may help the user understand that there may be no "good" options, just least bad options. For example, a patient with metastatic lung cancer may not have any A rated treatment options. Similarly, an otherwise healthy patient with a cold may not have any F rated options; as even watchful waiting is likely to resolve that condition without issues.

Each treatment regimen (224) may include a number of subratings (226). In an example, all the subratings (226) are displayed. In another example, a subset of the subratings (226) is displayed. The display may include an option to modify which subratings (226) are displayed. The subratings include outcome, reliability, and relevance. Other potential subratings are discussed above but may include other factors like side effects, cost, time commitment, etc.

Outcome is an assessment of the benefit from the treatment regimen (224). Outcome may be reported as a rating. Outcome may be reported as an amount of time, for example, increased life expectancy in cancer patients. Outcome may be reported as a decrease in pain and/or other undesirable impacts of the condition.

Reliability is a measure of the data available to support the findings of outcome. It is possible to have a treatment regimen (224) which is very reliable but produces little or no beneficial outcome. Similarly, it is possible to have an experimental treatment regimen (224) which has excellent outcomes but low reliability. In some examples, treatment regimens with a reliability rating below a threshold are marked as "Experimental" in the display. In FIG. 2, for example, Treatment 2 has a low reliability of 20% and is marked as EXPERIMENTAL. This provides notice to patients that the outcome is less reliable than other ratings. In another example, a treatment may be marked as EXPERIMENTAL if it is only supported by off-label use. Off label treatments may be marked as OFF-LABEL, again to provide notification to the user. Treatments with high reliability which represent the standard of care by be similarly marked STANDARD OF CARE. In an example, to receive the standard of care designation, the associated professional organization and/or an accrediting body may have to designate that treatment as standard of care. Many professional medical societies provide treatment guidelines which may be used to define a standard of care for a condition. A treatment may have multiple designations. For example, some treatments, for example in oncology, may be both OFF-LABEL and STANDARD OF CARE.

Relevance looks at the available data to support the treatment for a given patient. This is consideration of the patient factors, including other medical conditions, age, etc. when compared with the groups used to generate the reliability measurement. Many studies have exclusion/inclusion criteria which make it challenging to directly extrapolate the results to other populations. This is especially true of experimental, off-label, and/or newer treatments which may have evaluated a small population of patients. Relevance may be expressed as a number (e.g., 0% to 100%). Relevance may be expressed as categories (e.g., Acceptable data, Limited data, No data). Relevance may flag exclusion criteria from a study that apply to the patient. For example, if all the studies exclude patients under 50, then Relevance may flag this for a patient under 50. In contrast, if one study out of five, excludes patients under 50, then there may be adequate population of patients under 50 in the other four studies to assure relevance and to not flag the treatment regimen (224).

In some examples, a hypertext link (228) to a list of citations is available for each treatment regimen (224). The list of citations may be a bare list of citations. The list of citations may also include breakdowns of the cohorts described in the citation. The list of citations may include ratings, weightings, and/or other assessments of the citations. For example, the list of citations may be ordered by weighting. The list of citations may be ordered by number of patients and/or some other metric.

Near the bottom, buttons exist to modify the sorting order (230) by different ratings and/or subratings. The list may be sorted by the overall rating and/or by different sub-ratings. For example, the list may be sorted by: best outcome, best overall rating, highest relevance, etc. to aid the patient and/or medical professional make informed decisions about treatment regimens.

A button (232) allows also user to edit the patient factors (220). In an example, editing a patient factor (220) causes the system (200) to automatically recalculate the results based on the new information. The system (200) may wait until editing the patient factors (220) is complete prior to recalculating the results. The system (200) may include a button and/or other command to start recalculation of the results. In some examples, recalculation of the results is used to modify the relevance and overall ratings but does not impact some subratings.

The system (200) may perform a search of a database to determine if additional documents are available. In some examples, a search is performed automatically when a patient factor is updated. In another example, there is a command, e.g., a button, which causes the system to check for new information. The system (200) may also perform periodic searches on a variety of medical conditions, process any new documents identified, and store the results in a database. The database may be local. The database may be remote. In one example, the remote database is shared by a number of instances of the computer program product. This may speed the responsiveness to user requests as some of the analysis and data extraction may be performed in advance. In an example, this reduces the time between identifying attributes of the patient (112) and the system (200) providing (118) a recommendation for a treatment regimen based on the attributes of the patient.

Figure 3:
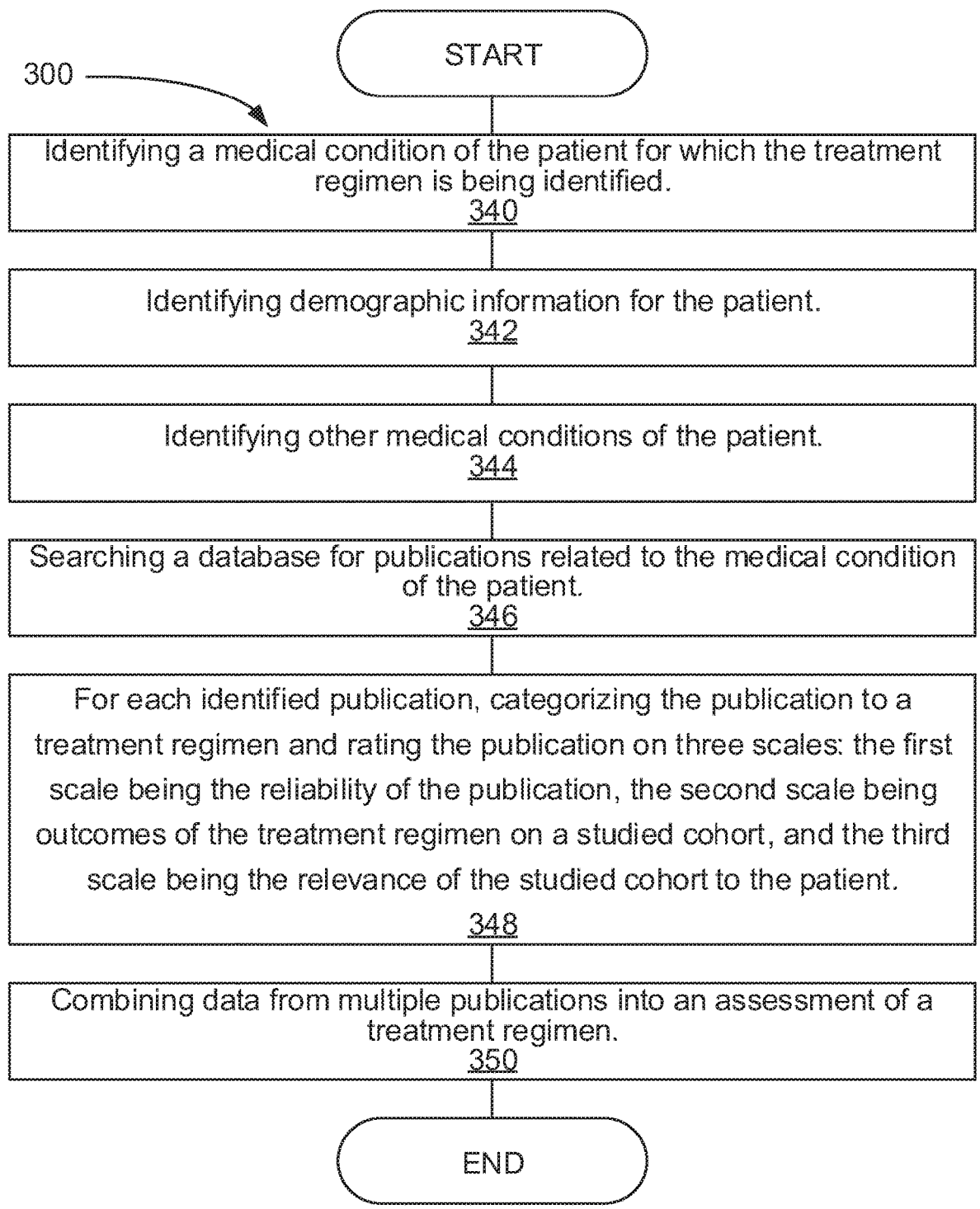
FIG. 3 shows a flowchart of a computer-implemented method consistent with this specification.

FIG. 3 shows a flowchart of a computer-implemented method (300) of identifying a treatment regimen for a patient. The method (300) including: identifying (340) a medical condition of the patient for which the treatment regimen is being identified: identifying (342) demographic information for the patient: identifying (344) other medical conditions of the patient; searching (346) a database for publications related to the medical condition of the patient; for each publication, categorizing (348) the publication to a treatment regimen and rating the publication on three scales (350): the first scale (350-1) being the reliability of the publication, the second scale (350-2) being outcomes of the treatment on a studied cohort, and the third scale (350) being the relevance of the studied cohort to the patient; and combining (352) data from multiple publications into an assessment of a treatment regimen.

The method (300) includes identifying (340) a medical condition of the patient for which the treatment regimen is being identified. The medical condition may be a disease. The medical condition may be a condition. The medical condition may be temporary and/or long term. In some examples, the medical condition is extracted from a chart and/or a charting application. For example, the method (300) may include identifying an entry in a chart by a medical professional and performing the other operations to recommend a treatment regimen (244). The method (300) may include identifying a condition associated with an appointment for a patient and identifying potential treatment regimens (244) prior to confirmation of the diagnosis of the condition by the patient. For example, a patient may identify a medical condition when making an appointment. Similarly, many intake forms include a reason for appointment area. Identifying treatment regimens based on this information makes it available to the medical professional during the appointment, assuming the diagnosis is correct. If the original diagnosis is erroneous, then there may be a delay in providing treatment options for the medical provider and/or patient to review.

The method (300) includes identifying (342) demographic information for the patient. Demographic information may include age, gender, living situation, socio economic status, etc. As used herein, demographic information is different from medical conditions, which refer to diagnosable medical conditions. However, with factors like age, the dividing line is not always clear.

The method (300) includes identifying (344) other medical conditions of the patient. The other medical conditions may be identified from a medical history taking by a medical professional. The other medical conditions may be identified by an intake form. The other medical conditions may be identified and/or diagnosed by a medical professional. In some examples, the patient is asked to review the medical conditions to prompt for any missed items. In some examples, the identification includes review of a patient's medical records at the institution.

The method (300) includes searching (346) a database for publications related to the medical condition of the patient. The database may include journal articles, review articles, letters, case histories, etc. In some examples, white papers from the associated organization are included in the database documenting outcomes at the institution.

The method (300) includes for each publication, categorizing (348) the publication to a treatment regimen. A publication may include treatment groups from multiple treatment regimens. For example, it is not uncommon to see both a high and a low dose of a medication with a shared control arm. In such cases, the cohorts may be broken out into multiple treatment regimens. It is also useful to identify the control arm. In many cases, control arms are not placebo but rather are standard of care (SoC). In such instances, the publication may help identify standard of care and/or provide additional data to support standard of care treatment regimen.

The method (300) includes rating each categorized publication on three scales (350): the first scale (350-1) being the reliability of the publication, the second scale (350-2) reports outcomes of the treatment on a studied cohort, and the third scale (350) reports the relevance of the studied cohort to the patient. The first rating on the first scale (350-1) provides an assessment of the quality of the documented study. The second rating on the second scale (350-2) assesses the outcome of the treatment regimen. As discussed above, different metrics for outcomes are used in different fields of medical. Accordingly, the rating of the second scale (350-2) may be in a specific metric and/or in a generalized value. The third rating on the third scale (350-3) looks at similarity and differences between the patient and the cohort used to generate the data in the publication. This third scale may consider inclusion and/or exclusion criteria for the documented results. The third scale may consider comorbidities, demographic match and other factors. The third scale seeks to answer the question, how reasonable is extrapolation of the data from the study to this particular patient, based on the information known about this patient and the cohort of the study?

The method (300) includes combining (352) data from multiple publications into an assessment of a treatment regimen. While large scale studies are very valuable for the insights they provide, they are also relatively rare and expensive. Accordingly, combining results from multiple reports and/or studies may be used to provide a broader assessment of a treatment regimen. Such combinations may also provide a sense of institution to institution variation. Such combined reports are sometimes referred to as meta-analyses and/or reviews. In some examples, the method (300) includes excluding either the base references and/or an associated meta-analysis to avoid double counting results.

The relevance rating may result from comparison of patient characteristics including patient demographic information and medical conditions with exclusion and inclusion conditions from the publication. The relevance rating may depend on the fit of the patient based on the patient demographic information and medical conditions with a cohort described in the publication.

The method (300) may further include sorting treatment regiments (244) by an elected scale of the three scales. In some examples, the system includes a setting allowing a user to select and/or change the sorting scale(s). In an example, the system includes buttons, toggles, and/or similar features to select the basis for sorting displayed treatment regimens (244).

The reliability rating may consider a cohort size documented in a publication. The reliability rating may consider the statistical confidence levels (e.g., p-scores of outcomes) in the publication.

The method (300) may further include excluding a publication comprising a data set or a meta-analysis the data set when a publication comprising the data set or meta-analysis is included. This avoids a single set of results being double counted for purposes of analysis.

The method (300) may further include saving search parameters and/or outcomes of the search and modifying parameters of a subsequent search based on an outcome of the search.

Figure 4:
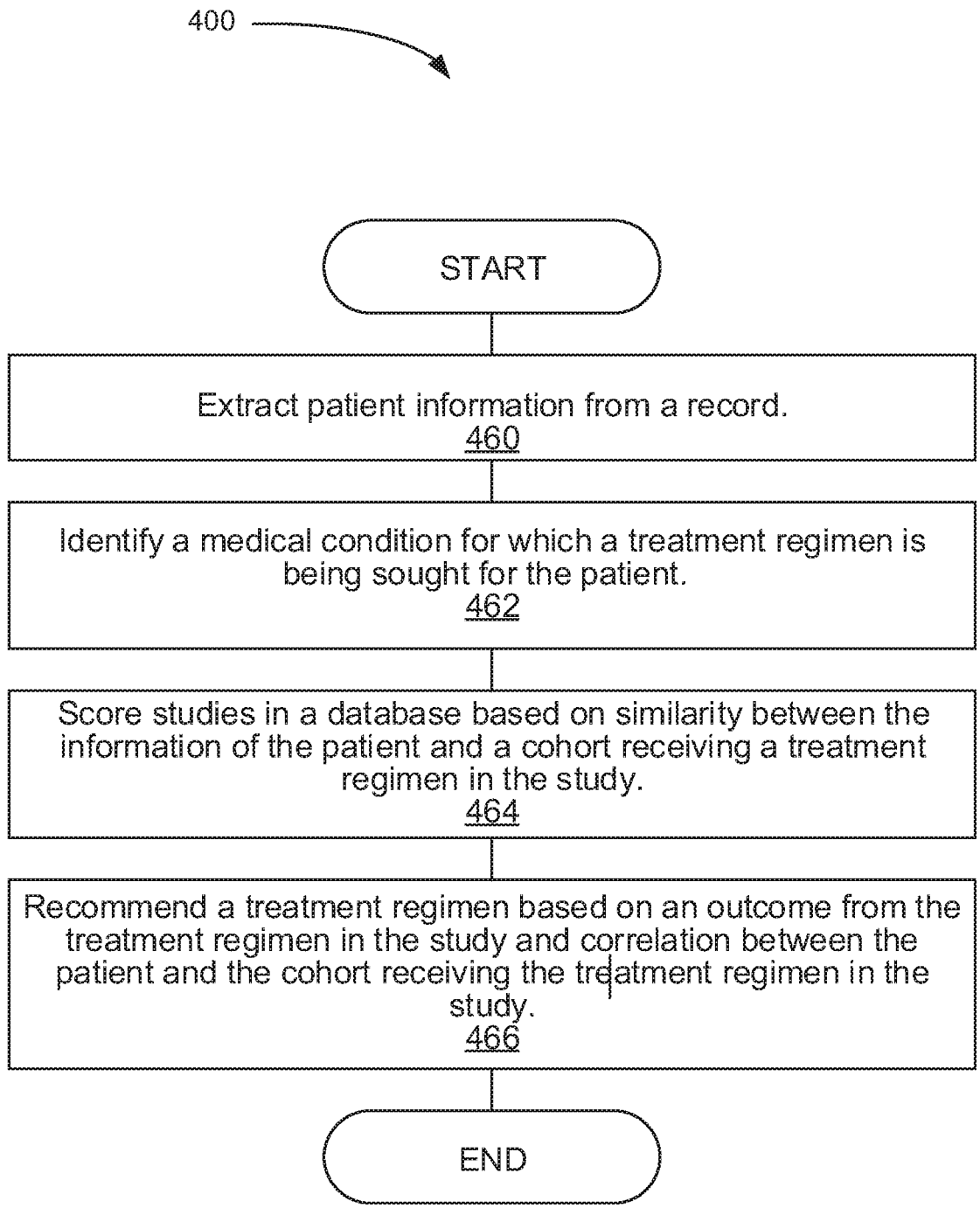
FIG. 4 shows a flowchart for a computer program product for identifying a patient specific treatment regimen consistent with this specification.

FIG. 4 shows a flowchart for a computer program product for identifying a patient specific treatment regimen consistent with this specification. The program product comprising a computer readable storage medium having program instructions embodied therewith, the program instructions readable by a processor to cause the processor to: extract (460) patient information from a record; identify (462) a medical condition for which a treatment regimen is being sought for the patient; score (464) studies in a database based on similarity between the information of the patient and a cohort receiving a treatment regimen in the study; and recommend (466) a treatment regimen based on an outcome from the treatment regimen in the study and correlation between the patient and the cohort receiving the treatment regimen in the study.

The computer extracts (460) patient information from a record. The record may be a medical record. The record may be an appointment record. The record may be a medical chart, physical and/or electronic.

The computer identifies (462) a medical condition for which a treatment regimen is being sought for the patient. The medical condition may be explicitly provided by a medical professional. The medical condition may be provided by a patient. The medical condition may be reported in an appointment summary. The medical condition may be provided by an admission form and/or medical history.

The computer scores (464) studies in a database based on similarity between the information of the patient and a cohort receiving a treatment regimen in the study. The studies are studies of treatment regimens for the identified condition. The computer scores them to identify the relevance of the cohorts in the studies to the patient.

The computer recommends (466) a treatment regimen based on an outcome from the treatment regimen in the study and correlation between the patient and the cohort receiving the treatment regimen in the study. The recommendation considers both outcome and relevance of the studies to the patient. The recommendation may further consider other factors, including, the size of the cohort in the study, the p-value of the results in the study, the publication quality, the number of citations to the study, the total number of studies of the treatment regimen, the current standard of care, etc.

What is claimed is:

1. A computer-implemented method comprising:
a processor identifying a medical condition of a patient;
the processor identifying attributes of the patient;
the processor searching a database for treatment regimens for the medical condition;
the processor scoring identified treatment regimens based on outcomes and similarity of the attributes of the patient to cohorts treated with the treatment regimens, wherein similarity of the attributes of the patient to a cohort treated with a specific treatment regimen is assessed against inclusion criteria for the cohort associated with the specific treatment regimen and similarity is discounted based on a number of standard deviations by which at least one said attribute of the patient differs from a cohort mean value for the at least one said attribute in the specific treatment regimen; and
the processor providing a recommendation for a treatment regimen for the patient based on the scoring.

2. The computer-implemented method of claim 1, wherein scoring includes an assessment of article quality.

3. The computer-implemented method of claim 2, wherein the assessment of article quality includes a number of citations to the article.

4. The computer-implemented method of claim 1, wherein scoring includes an assessment of publication quality.

5. The computer-implemented method of claim 1, further comprising, when an amount of search results are outside a window, modifying parameters of the search and repeating the search with modified parameters.

6. The computer-implemented method of claim 1, further comprising accessing documented search parameters and results to search the database.

7. A computer program product for identifying a treatment regimen for a patient based on medical conditions of the patient and demographic information of the patient the computer program product comprising a computer readable storage medium having program instructions embodied therewith, wherein the computer readable storage medium is not a transitory signal per se, the program instructions readable by a computer to cause the computer to perform a method comprising:
identifying a medical condition of the patient for which the treatment regimen is being identified;
identifying demographic information for the patient;
identifying other medical conditions of the patient;
searching a database for publications related to the medical condition of the patient;
for each identified publication, categorizing the publication to a treatment regimen and rating the publication on three scales:
the first scale being the reliability of the publication,
the second scale being outcomes of the treatment regimen on a studied cohort, and
the third scale being a relevance of the studied cohort to the patient; and
combining data from multiple publications into an assessment of a treatment regimen by combining simulations of cohorts in the multiple studies into a combined simulated cohort, wherein a relevance of the simulated cohort to the patient depends on a difference, in standard deviations, in a criterion of the patient and a mean value for the criterion for the simulated cohort, and
displaying values of the three scales to a user along with a recommended treatment regimen associated with the displayed values.

8. The computer program product of claim 7 wherein a publication documents more than one treatment regimen.

9. The computer program product of claim 7, wherein a relevance rating comprises comparison of patient characteristics including patient demographic information and medical conditions with exclusion and inclusion conditions from the publication.

10. The computer program product of claim 7, further comprising sorting treatment regiments by an elected scale of the three scales.

11. The computer program product of claim 7, wherein rating of reliability depends on a cohort size documented in a publication.

12. The computer program product of claim 7, further comprising excluding a publication comprising a data set or a meta-analysis of the data set when a second publication comprising the data set or meta-analysis is included.

13. The computer program product of claim 7, further comprising saving search parameters and outcomes of a first search and modifying parameters of a subsequent search based on an outcome of the first search.

14. A computer program product for identifying a patient specific treatment regimen the computer program product comprising a computer readable storage medium having program instructions embodied therewith, the program instructions readable by a processor to cause the processor to:
extract patient information from a record;
identify a medical condition for which a treatment regimen is being sought for the patient;
score studies in a database based on:
similarity between the information of the patient and a cohort receiving a treatment regimen in the study; and
a size of a treatment cohort in the study; and
recommend a treatment regimen based on an outcome from the treatment regimen in the study and correlation between the patient and the cohort receiving the treatment regimen in the study, wherein similarity is discounted based on a number of standard deviations between a patient value for a criterion and a mean for a cohort of the criterion.

15. The computer program product of claim 7, wherein combining data from multiple publications into an assessment of a treatment regimen comprises combining cohort size and characteristics from the multiple publications.

16. The computer-implemented method of claim 1, wherein a first treatment regimen of the treatment regimens is identified as standard of care in a display.

17. The computer-implemented method of claim 1, wherein similarity of the attributes of the patient to cohorts treated with a treatment regimen is determined using principle component analysis (PCA).

18. The computer-implemented method of claim 1, wherein the processor searching the database for treatment regimens for the medical conditions comprises accessing search parameters from a previous search.

19. The computer-implemented method of claim 1, wherein a first treatment regimen of the treatment regimens is identified as off label in a display.

20. The computer-implemented method of claim 1, wherein each treatment regimen is scored by three scales:
- the first scale being a reliability of the publication,
- the second scale being outcomes of the treatment regimen on a studied cohort, and
- the third scale being the relevance of the studied cohort to the patient; and
- wherein values of the three scales are displayed with a recommended treatment regimen.

\* \* \* \* \*